United States Patent [19]

Suzuki

[11] 4,126,614
[45] Nov. 21, 1978

[54] OXACAPROLACTAMS

[75] Inventor: Shigeto Suzuki, San Francisco, Calif.

[73] Assignee: Chevron Research Company, San Francisco, Calif.

[21] Appl. No.: 890,360

[22] Filed: Mar. 27, 1978

Related U.S. Application Data

[63] Continuation-in-part of Ser. No. 826,490, Aug. 22, 1977, abandoned.

[51] Int. Cl.$^2$ .................. C07D 267/12; C07D 273/00
[52] U.S. Cl. ........................... 260/239.3 R; 260/30.2; 562/567
[58] Field of Search ................................. 260/239.3 R

[56] References Cited

U.S. PATENT DOCUMENTS 2,771,468  11/1956  Surrey .................... 260/239.3 R Primary Examiner—Henry R. Jiles
Assistant Examiner—Robert T. Bond
Attorney, Agent, or Firm—D. A. Newell; John Stoner, Jr.

[57] ABSTRACT 3-oxacaprolactam is prepared by a process which comprises: contacting an organic acid anhydride solution of a cyanoalkoxyalkanoate with hydrogen in the presence of a noble metal hydrogenation catalyst to prepare an amide-ester; and heating the amide-ester in excess water at a temperature above about 200° C.

10 Claims, No Drawings

OXACAPROLACTAMS

CROSS-REFERENCE TO RELATED APPLICATIONS

This application is a continuation-in-part application of application Ser. No. 826,490, filed Aug. 22, 1977, now abandoned.

BACKGROUND OF THE INVENTION

This invention concerns the preparation of oxacaprolactams by hydrogenation of cyanoalkoxyalkanoates and hydrolysis of the resulting amide-ester. In particular, this invention concerns 3-oxacaprolactams and their preparation.

The 3-oxacaprolactams of this invention have the formula

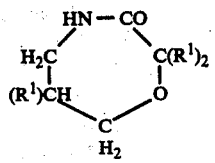

wherein each $R^1$ is hydrogen or methyl. Compounds having this formula can be polymerized by either anionic polymerization or hydrolytic polymerization to prepare low molecular weight hydrophilic polyamides. These low molecular weight polymers have a relatively low melting point, and at room conditions are sticky, rubbery materials useful as resueable adhesive caulking agents.

Caprolactam has been obtained by the dehydrogenation of cyclohexanol to cyclohexanone which is then converted to the oxime and rearranged to form the lactam:

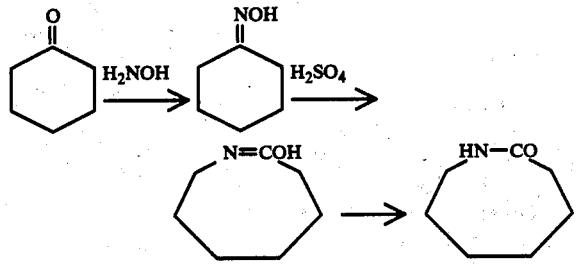

The lactam, containing a seven-membered ring, can be converted to a linear polymer by heating with a trace of water:

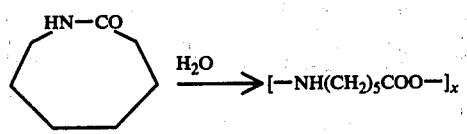

The polymer of caprolactam is nylon-6.

Various polyamides can be polymerized or copolymerized to prepare fibers having different properties. For example, German Published Offenlegungstag, 2,454,118 (May 15, 1975) describes a hydrophilic polyamide prepared by copolymerizing adipic acid and a diamine having the structure $(CH_2-O-(CH_2)_3-NH_2)_2$.

The diamine was prepared by cyanoethylation of ethylene glycol followed by hydrogenation. The hydrophilicity of the polymer is likely due to the presence of oxygen in the recurring unit.

SUMMARY OF THE INVENTION

It has now been found that 3-oxacaprolactams can be prepared by hydrogenation and ring cyclization of betacyanoalkoxyalkanoates. The process comprises contacting a carboxylic acid anhydride solution of a cyanoalkoxyalkanoate with hydrogen in the presence of a noble metal hydrogenation catalyst, preferably at a temperature of from about 20° C. to about 60° C., to form an amide-ester; and heating the amide-ester in excess water at a temperature above about 200°;0 C. The preferred starting material is methyl beta-cyanoethoxyacetate.

DETAILED DESCRIPTION OF THE INVENTION

The 3-oxacaprolactams provided by this invention have the formula

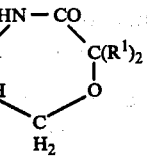

wherein each $R^1$ is independently hydrogen or methyl. Unsubstituted 3-oxacaprolactam, wherein each $R^1$ is hydrogen, has a melting point of 60° C. and a boiling point of 133° C./5 mmHg.

The oxacaprolactams depicted above are prepared by a two-step process. In the first step, a carboxylic acid anhydride solution of a cyanoalkoxyalkanoate is hydrogenated and acylated to prepare the corresponding amide ester. The cyanoalkoxyalkanoate staring materials can be prepared by cyanoethylation or cyanopropylation of hydroxy acetic acids according to the procedure described in copending U.S. patent application Ser. No. 763,279, filed Jan. 27, 1977. Preferred cyanoalkoxyalkanoates include, for example, compounds of the formula

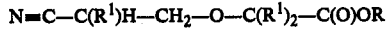

$N\equiv C-C(R^1)H-CH_2-O-C(R^1)_2-C(O)OR$ wherein each $R^1$ is independently hydrogen or methyl and R is hydrogen, $C_1$ to $C_6$ lower alkyl, 2-hydroxyethyl, or 2-(2-hydroxyethoxy)ethyl. Methyl-2-cyanoethoxyacetate is particularly preferred.

The hydrogenation of the cyano-ester is carried out in a carboxylic acid anhydride solution in the presence of a noble metal hydrogenation catalyst. At least one equivalent of anhydride per cyano group is required. Preferably excess anhydride is used. Among other factors, the success of the process is due to the discovery that under select conditions the hydrogenation reaction can be carried out without significant decomposition of the ester. It has been found that, although the Raney metal hydrogenation catalysts, such as Raney cobalt, decomposed the ester before hydrogenation could take place, the noble metal hydrogenation catalysts produced excellent yields of the desired amide-ester. The noble metal hydrogenation catalysts are well known in the hydrogenation art. As used herein the term "noble metal" includes ruthenium, rhodium, palladium, osmium, iridium and platinum. Platinum catalysts are particularly active. The hydrogenation is carried out in a carboxylic acid anhydride solution of the cyanoalkoxyacetate. Acetic acid anhydride is the preferred solvent; however, any of the usual organic acid anhydride solvents are suitable alone or in combination. The anhydride may be diluted with up to about 80% (by weight) of a low molecular weight carboxylic acid. The preferred acid is acetic acid. For example, suitable solvents include acetic anhydride, propionic anhydride, acetic propionic anhydride, acetic anhydride-acetic acid mixture, etc.

The usual hydrogenation conditions are suitable. Hydrogen partial pressures of from about 25 psig to 5000 psig have given good yields. The temperature can vary from ambient to 80° C.; preferably the solution is maintained at a temperature between about 20° C. and 60° C. Very high yields of hydrogenated product, on the order of 98%, have been obtained at a temperature of about 45° C. and a hydrogen pressure of about 60 psig. As the temperature is increased, the hydrogen uptake increases. Accordingly, shorter contact times can generally be obtained at higher temperatures. Typically, a contact time of from 5 hours to 20 hours is sufficient to give above 80% yields of hydrogenated product.

The product of the hydrogenation of the cyanoester is an amide-ester. The stoichiometry of the reaction is:

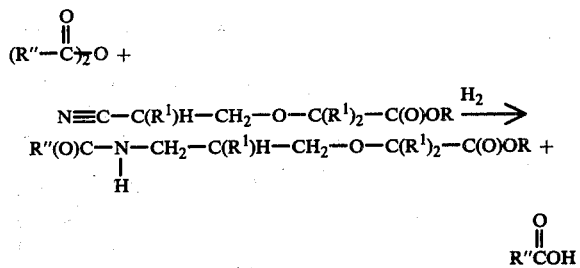

wherein R and R' are as previously defined and R" is an alkyl group of 1 to 5 carbon atoms. For example, where methyl 2-cyanoethoxyacetate is the starting ester and acetic anhydride is the solvent, the amide-ester product is methyl N-acetyl-6-amino-3-oxacaproate. The amide-ester can be removed by conventional separation methods. For example, the amide ester can be recovered by filtration and distillation.

In the second step of the process provided by this invention, the amide-ester produced by hydrogenation of the cyano-ester is cyclized by hydrolysis. The hydrolysis reaction is carried out by heating the amide-ester in a hydroxylic solvent at a temperature above about 200° C. Typical hydroxylic solvents include water, ethanol, ethylene glycol, methanol or mixtures thereof. Water is preferred.

The hydrolysate product, after removal of the hydroxylic solvent, comprises the oxacaprolactam, 6-amino-oxacaproic acid and its cyclic oligomers and linear oligomers. The oxalactam product can be separated by conventional methods. For instance, the acid and linear oligomers can be removed by extraction of the oxalactam and cyclic oligomers using chloroform. The extract can then be fractionally distilled to obtain the oxalactam as a distillate and the remainder as a distillation residue. The oxalactam can be purified by recrystallization from benzene.

EXAMPLE

The following example further illustrates the invention. Modifications of the example within the scope of the following claims will be apparent.

I. Preparation of Methyl N-Acetyl-6-Amino-3-Oxahexanoate

Methyl 2-cyanoethoxyacetate was hydrogenated to prepare methyl N-acetyl-6-amino-3-oxahexanoate.

14.3 grams of the cyano-ester in about 0.42 equivalents of acetic anhydride were added with about 1 weight percent of platinum dioxide catalyst to a pressure vessel. The vessel was pressurized with from about 60 to 80 psig hydrogen and heated to about 50° C. to 57° C. for 18 hours. Filtration and distillation of the hydrogenation product gave 87 mol percent of methyl N-acetyl-6-amino-3-oxahexanoate having a boiling point of about 125° C. at 0.06 mm Hg vacuum and a melting point of 27°–32° C. The infrared spectra showed strong absorbance at 1745 $cm^{-1}$ (ester carbonyl) and at 1660 $cm^{-1}$ (amide carbonyl). The NMR spectra were consistent with the assigned structure.

II. Preparation of 3-Oxacaprolactam (a) 50 grams of methyl N-acetyl-6-amino-3-oxahexanoate, prepared by the method described above was hydrolyzed by heating with 600 grams of water at 265° C. for 2½ hours. Water was removed on a rotary evaporator to leave 44.8 grams of a crude product. This material was extracted three times with 200 ml portions of chloroform. The chloroform extracts were combined and evaporated to give 20.9 grams of material. This material was distilled at 5 mm Hg to give 7.3 grams of overhead having a boiling point of 132°–137° C. From this overhead, 4.55 grams of 3-oxacaprolactam crystallized and were recovered by centrifugation. The product had a melting point of 60° C. after recrystallization from benzene. The mass spectra of the compound gave a molecular weight of 115 (theoretical 115). The infrared spectra had strong absorbance at 3280 $cm^{-1}$ (NH stretching), and at 1660 $cm^{-1}$ (amide carbonyl). The NMR spectra were consistent with the assigned structure. Analysis calculated for $C_5H_9NO_2$: C, 52.2; H, 7.8; N, 12.2%. Found: C, 53.2; H, 8.0; N, 12.4%.

Other runs were carried out in a manner similar to Example II. These are summarized in Table I.

TABLE I

| Run No. | Amide-Ester (grams) | Hydroxylic Solvent, (grams) | Temp. °C | Time (hrs.) | Yield of Oxacaprolactam (mol %) |
|---|---|---|---|---|---|
| II(b) | 50 | water, 600 | 260 | 2 | 19.2[1] |
| II(c) | 50 | water, 600 | 260 | 2 | |
| II(d) | 0.7 | water, 7 | 260 | 2 | 41.2 |
| II(e) | 0.7 | water, 7 | 260 | 1 | 36.5 |
| II(d) | 0.7 | water, 7 | 200 | 1 | 24.3 |
| II(e) | 0.7 | water, 7 | 200 | 2 | 13.2 |
| II(f) | 0.7 | water, 3.5 ethanol, 3.5 | 260 | 1 | 53.6 |
| II(g) | 0.7 | water, 35 | 260 | 1 | 45.6 |

[1]Isolated Yield.

The residues remaining after chloroform extractions from several runs were combined and allowed to stand for seven days. At the end of that time, crystals had formed and were separated by centrifugation. The crystals were identified as 6-amino-3-oxahexanoic acid, m.p. 184°–185° C. (dec). The infrared spectra had strong absorbance at 1720 cm $^{-1}$ (carboxylic carbonyl). The NMR spectra were consistent with the assigned structure.

Hydrolysis of Distillation Bottoms

The distillation bottoms from combined Runs II(b) and (c), 11.9 grams were refluxed for 24 hours with 100 ml of concentrated hydrochloric acid. At the end of this time the aqueous hydrogen chloride was removed by evaporation to give 11.6 grams of solids. This solid was dissolved in 100 ml of water and passed over a basic ion exchange resin. The effluent from this treatment was evaporated to dryness to give 5.4 grams of crystalline 6-amino-3-oxahexanoic acid having a m.p. of 184°–185° C. (dec). (recrystallized from ethanol/acetone solvent).

This experiment indicates that the distillation bottoms were oligomers of 6-amino-3-oxahexanoic acid.

The bottoms from the distillation of combined Runs II(b) and (c), 6.7 grams were dissolved in 50 ml of 1-propanol. The solution was cooled to effect crystallization. The crystals were collected by filtration and dried to give 1 gram of product having a m.p. of 208°–211° C. A mass spectra analysis gave the molecular weight of 230, corresponding to a cyclic head-to-tail dimer of 6-amino-3-oxahexanoic acid, 3,10-dioxa-7,14-diazacyclotetradecane-1,8-dione:

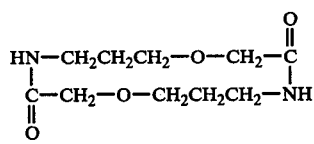

Infrared analysis gave strong absorbance at 3430 cm$^{-1}$, (NH stretching in secondary amide), 1670 cm$^{-1}$, (amide carbonyl), 1545 cm$^{-1}$, (amide II bond), and 1112 cm$^{-1}$ (ether). The NMR spectra agreed with the assigned structure.

Preparation of 3-Oxacaprolactam from the Amino Acid

A 15 ml microbomb was charged with 1 gram of 6-amino-3-oxahexanoic acid and 8 grams of absolute ethanol. This mixture was heated at 200° C. for 1 hour. At the end of this time the crude reaction product was analyzed by gas chromatography and found to contain 3-oxacaprolactam.

Polymerization of 3-Oxacaprolactam

I. Anionic Polymerization 3-oxacaprolactam was polymerized under standard anionic polymerization conditions by heating 5.5 grams of 3-oxacaprolactam in the presence of 0.062 gram of 1% potassium pyrrolidonate and 0.063 gram of 1% N-acetyl-pyrrolidone at 150° C. for 6.5 hours. The resulting polyoxacaprolactam was a sticky, viscous, orange-colored, water-soluble material having a molecular weight of about 4000 and a melting point of about 75° C.

II. Hydrolytic Polymerization 3-oxacaprolactam was polymerized under standard hydrolytic polymerization conditions by heating 3.26 grams of 3-oxacaprolactam in the presence of 36 milligrams of water at 255° C. for 21 hours under a nitrogen atmosphere. The resulting polyoxacaprolactam was a sticky, viscous, orange-colored material having a molecular weight of about 1200 and a melting point of about 91° C.

What is claimed is:

1. A process for preparing a compound of the formula

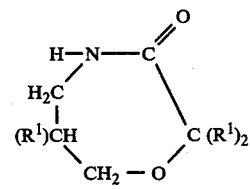

wherein each R$^1$ is hydrogen or methyl which comprises contacting a carboxylic acid-anhydride solution of a compound of the formula

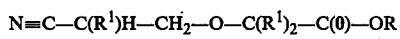

N≡C—C(R$^1$)H—CH$_2$—O—C(R$^1$)$_2$—C(0)—OR where R is hydrogen, lower alkyl, hydroxyethyl or 2-(2-hydroxyethoxy)ethyl and each R$^1$ is hydrogen or methyl with hydrogen in the presence of a noble metal hydrogenation catalyst to prepare an amide-ester, and heating the amide-ester in excess water at a temperature above about 200° C.

2. A process in accordance with claim 1 wherein the cyanoalkoxyalkanoate is methyl-2-cyanoethoxyacetate.

3. A process in accordance with claim 1 wherein the cyanoalkoxyalkanoate is in solution with acetic acid anhydride.

4. A process in accordance with claim 1 wherein the catalyst is a platinum catalyst.

5. A process in accordance with claim 1 wherein the process is carried out at a temperature of from about 20° C. to about 60° C.

6. A process for preparing 3-oxacaprolactam which comprises: contacting methyl-2-cyanoethoxyacetate in excess acetic acid anhydride with hydrogen in the presence of a catalytic amount of platinum to prepare N-acetyl-6-amino-3-oxamethylhexanoate, and heating in excess water at a temperature of about 260° C.

7. A process in accordance with claim 6 wherein methyl-2-cyanoethoxyacetate is contacted at a temperature of about 45° C.

8. A compound of the formula

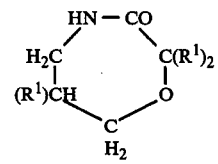

wherein each R$^1$ is hydrogen or methyl.

9. 3-oxacaprolactam.

10. 3,10-dioxa-7,14-diazacyclotetradecane-1,8-dione.